United States Patent
Ohishi et al.

(10) Patent No.: US 8,425,949 B2
(45) Date of Patent: Apr. 23, 2013

(54) EXTERNAL USE COMPOSITION FOR SKIN

(75) Inventors: Hifumi Ohishi, Tokyo (JP); Keizou Ohishi, Saitama (JP); Tetsuya Oishi, Tokyo (JP); Hisanori Tani, Tokyo (JP)

(73) Assignee: Hydrox, Inc., Saitama (JP)

( * ) Notice: Subject to any disclaimer, the term of this patent is extended or adjusted under 35 U.S.C. 154(b) by 0 days.

(21) Appl. No.: 13/289,648

(22) Filed: Nov. 4, 2011

(65) Prior Publication Data

US 2012/0114690 A1 May 10, 2012

(30) Foreign Application Priority Data

Nov. 4, 2010 (JP) ................................. 2010-247525

(51) Int. Cl.
*A01N 65/00* (2009.01)

(52) U.S. Cl.
USPC ......................................................... 424/725

(58) Field of Classification Search ........................ None
See application file for complete search history.

(56) References Cited

FOREIGN PATENT DOCUMENTS

| | | |
|---|---|---|
| JP | H03-258709 | 11/1991 |
| JP | H03-258710 | 11/1991 |
| JP | 2004-229534 | 8/2004 |
| JP | 2008-120738 | 5/2008 |

OTHER PUBLICATIONS

Amellal, et al. (1985) "Inhibition of mast cell histamine release by flavonoids and bioflavonoids." *Planta. Med.* 1:16.
Chakravarty, N. (1980) "The role of plasma membrane $Ca^{++}$, $Mg^{++}$ activated adenosine triphosphatase of rat mast cells on histamine release." *Acta Pharmacol. Toxicol.* 47:223.
Cheong, et al. (1998) "Studies of structure activity relationship of flavonoids for the anti-allergic actions," *Arch. Pharm. Res.* 21:478.
Fewtrell, et al. (1977) "Effect of flavone inhibitors of transport ATPases on histamine secretion from rat mast cells." *Nature* 265:635.
Kotani, et al. (1999) "Allergy inhibition effects of persimmon leaf extracts in human basophilic leukocytes and mouse." *Journal of Japan Society of Nutrition and Food Sciences* 52(3):147.

*Primary Examiner* — Michael Meller
(74) *Attorney, Agent, or Firm* — Harness, Dickey & Pierce, P.L.C.; J. Timothy Keane; Kisuk Lee

(57) ABSTRACT

The present disclosure provides an external use composition for skin comprising a tarajo holly leaf extract and a Japanese knotweed leaf extract, a brown algae extract and an egg shell membrane derived peptide (ESM-P) having a molecular mass of 3 kDa or higher. The composition according to the present invention can be used to treat a disease or condition of skin relating to a filaggrin metabolism anomaly, such as atopic dermatitis. The composition according to the present invention can be used specifically for the therapy of atopic dermatitis.

10 Claims, 1 Drawing Sheet

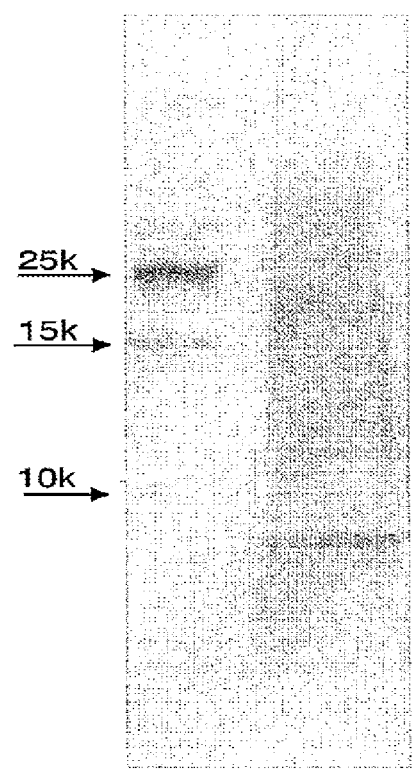

EXTERNAL USE COMPOSITION FOR SKIN

CROSS-REFERENCE TO RELATED APPLICATION

This application claims the benefit of and priority to Japanese Patent Application No. 2010-247525 filed Nov. 4, 2010. The entire disclosure of the above application is incorporated herein by reference.

FIELD

The present invention relates to an external agent for skin. The external agent for skin of the present invention has an effect of reducing and eliminating itches and pains by inhibiting histamine release and cyclooxygenase (COX)-2 activity, an effect of regulating excessive immune response by inhibiting cytokine generation, and an effect of normalizing epidermis formation by accelerating filaggrin synthesis. The agent of the present invention is effective for various refractory skin diseases, specifically atopic dermatitis.

BACKGROUND

Pathological conditions of atopic dermatitis, which is a refractory skin disease, include a nonallergic mechanism and an allergic mechanism. The former mechanism is represented by skin barrier dysfunction, and the latter mechanism is caused by an immune disorder. However, these pathological conditions cannot be strictly divided, since genetic factors and environmental factors causing the conditions are intricately interwound. Atopic dermatitis is induced and/or aggravated not only by genetic factors, but also by nonallergic factors, such as dry skin, and further by an immune disorder.

Understanding of refractory skin diseases, such as atopic dermatitis, is recently expanding. The current understanding is that the allergic mechanism includes an excessive release of histamine and an excessive secretion of protease and other substances due to the abnormal activation of mast cells and antigen-presenting cells at the affected area. It also includes an accelerated secretion of Th2 cell based interleukins, that is, IL-4, IL-5 and IL-13. Histamine causes the characteristic itch at the skin disease area. In addition, the increase of IL-4, IL-5 and IL-13 prevents the development of filaggrin, which is a skin barrier related protein, and of LL37, β-defensin-2, and β-defensin-3 exhibiting anti-microorganism activities, so the skin becomes vulnerable to microbial infection. The nonallergic mechanism is known to include increases in NADPH-oxidase and COX-2 activations according to an increase in sphingosyl phosphorylcholin in the corneal layer of the affected area, which increase the reaction products, that is, reactive oxygen species (ROS) and PG (prostaglandin) $E_2$. These products also significantly inhibit filaggrin synthesis.

Meanwhile, it is traditionally known that an egg shell membrane (ESM) has advantageous effects, such as reducing inflammation and accelerating epithelium formation, when it is stuck on the area affected by a burn, a cut, a laceration or other injuries. An expectation for utilizing ESM effects has led to the development of various external agents. Specifically, Patent Document 1 teaches cosmetics having soluble egg shell membranes and glycerophospholipid blended in them, and Patent Document 2 teaches cosmetics having soluble egg shell membranes and sphingolipid blended in them. These examples were developed as cosmetics having skin beautifying effects and moisturizing effects, based on synergistic effects of soluble egg shell membranes combined with other active ingredients. Further, the egg shell membrane hydrolysate applied externally or administered orally is known to accelerate collagen synthesis in the skin. Patent Document 3 teaches utilizing this effect in a drink containing a hydrolytic egg shell membrane as an active ingredient.

Meanwhile, the inventors of the present invention reported that the low molecular compounds (CCK) contained in extracts derived from seaweed belonging to the brown algae have effects of selectively inhibiting activation of COX-2 (Patent Document 4).

Tarajo holly (scientific name: *Ilex latifolia*) is a tall evergreen tree belonging to Aquifoliaceae *Ilex*, and its leaves have been brewed and drunk as health tea in China. Tarajo holly leaf extract has been used in foods for Type I allergy, such as pollinosis. This use is conventionally understood to be based on an antihistamic effect. However, recent studies revealed that the tarajo holly leaf extract contains fisetin as the main ingredient and inhibits IL-13 generation in vivo. Japanese knotweed (scientific name: *Fallopia japonica*) is a perennial plant belonging to Polygonaceae. Not only is its dried root (*Polygonum cuspidatum* root: kojoukon) brewed and used to treat constipation, urticaria and other diseases, but its young buds of early spring are used in food. The Japanese knotweed leaf extract contains a considerable amount of quercetin, and quercetin has allergy reduction and elimination effects based on antioxidation effects.

PATENT DOCUMENTS

Patent Document 1: Japanese Examined Patent Publication No. H06-047527 (Japanese Unexamined Patent Publication No. H03-258709)

Patent Document 2: Japanese Examined Patent Publication No. H06-047528 (Japanese Unexamined Patent Publication No. H03-258710)

Patent Document 3: Japanese Unexamined Patent Publication No. 2004-229534

Patent Document 4: Japanese Unexamined Patent Publication No. 2008-120738

SUMMARY

Skin diseases, such as atopic dermatitis, are often treated by using external use steroid and antiallergic drugs. Neither drug is etiotropic, that is, neither controls the cause of the symptoms. On the contrary, both drugs are nosotropic, that is, both drugs are mainly for eliminating or easing the superficial symptoms. Hence, terminating the administration of these drugs can cause the disease to recrudesce, and makes the disease chronic and refractory. Undesirable effects of these pharmaceutical agents are also known in the art. Accordingly, a safer agent having selectivity to different factors and high biocompatibility is called for.

As shown above, knowledge is being accumulated concerning skin diseases, such as atopic dermatitis, with a conclusion that these diseases are anomalies of filaggrin metabolism. IL-4, IL-5, IL-13, sphingosyl phosphorylcholine, ROS (a NADPH-oxidase reaction product) and $PGE_2$ (a COX-2 reaction product) are triggers of the disease. To remedy symptoms, it is necessary not only to eliminate triggers, but also to normalize filaggrin metabolism.

Accordingly, the object of the present invention is to provide external agents which not only have inhibition effects on histamine release from mast cells, IL-4, IL-5 and IL-13 generation inhibition effects and antioxidation effects, and selective cyclooxygenase COX-2 inhibition effects, but can effectively treat various refractory skin diseases, such as atopic dermatitis, by searching for ingredients exhibiting filaggrin synthesis accelerating effects and blending them into the agents.

The inventors of the present invention have been pursuing research and development of various functional materials derived from natural products. They found that the combination of extracts of tarajo holly leaves and Japanese knotweed leaves, brown algae extracts, and hen egg shell membrane hydrolysate are effective in achieving the above object, and completed an external use agent for skin containing such combination as an active ingredient. The present invention provides the following:

[1] A composition for skin comprising a tarajo holly leaf extract and a Japanese knotweed leaf extract, a brown algae extract, and an egg shell membrane derived peptide (ESM-P) having a molecular mass of 3 kDa or higher. In an embodiment, the composition is an external use composition.
[2] The composition according to [1] for treating a disease or condition of skin relating to a filaggrin metabolism anomaly.
[3] The composition according to [2] wherein the disease or condition of skin relating to the filaggrin metabolism anomaly is atopic dermatitis.
[4] The composition according to [3] for therapy of atopic dermatitis.
[5] An external use composition for skin consisting essentially of a tarajo holly leaf extract and a Japanese knotweed leaf extract.
[6] The composition according to [5] wherein the Japanese knotweed leaf extract is comprised at 0.5 to 2.0 weight parts to 1 weight part of the tarajo holly leaf extract.
[7] An agent for adding an external use composition for skin comprising a tarajo holly leaf extract and a Japanese knotweed leaf extract.
[8] The agent according to [7] for reducing or eliminating itches or pains, or for regulating cytokine generation.
[9] An external use composition for skin for treating a disease or condition of skin relating to filaggrin synthesis acceleration, wherein the composition comprises ESM-P.
[10] A filaggrin synthesis accelerator consisting essentially of ESM-P.
[11] A method for treating a disease or condition of skin relating to a filaggrin metabolism anomaly, other than a medical process, comprising the step of:
applying a composition comprising a tarajo holly leaf extract and a Japanese knotweed leaf extract, a brown algae extract and a bird egg shell membrane hydolysate to skin.
[12] The method according to [11] wherein the disease or condition of skin relating to the filaggrin metabolism anomaly is atopic dermatitis.

BRIEF DESCRIPTION OF THE DRAWING

FIG. 1 is a photograph of a SDS-PAGE of an egg shell membrane derived peptide (ESM-P) usable in the present invention. Its average molecular mass is about 8 kDa.

DETAILED DESCRIPTION

The present invention can improve immunological functions by inhibiting the release of histamine, which is a trigger in an allergic mechanism represented by atopic dermatitis, by inhibiting IL-4, IL-5, and IL-13 generation, and by inhibiting IgE generation. It can also improve filaggrin metabolism in the corneal layer, which is an aggravating factor of the non-allergic mechanism. The ingredients of the present invention do not show any severe side effects like steroid or other drugs, and they are quite safe. The above features work to remedy chronic skin diseases that are difficult to completely cure, such as atopic dermatitis.

The present invention provides an external use composition for skin including a tarajo holly leaf extract and a Japanese knotweed leaf extract, a brown algae extract and an egg shell membrane derived peptide (ESM-P) having a molecular mass of 3 kDa or more.

The expression "external use composition for skin" refers to a composition formed suitably for skin application, unless otherwise noted. It may comprise ingredients and various additives, other than the active ingredients, which are acceptable for external use on skin. The composition may be in the form of medical drugs or cosmetics. Additionally, when each active ingredient of the present invention is referred to as an "agent" alone or in combination with other ingredients, the expression indicates that the agent is an ingredient to be added to the external use composition for skin, unless otherwise noted. The "agent" of the present invention includes neither a medical product per se nor a cosmetic per se, unless otherwise noted.

Active Ingredients

The composition according to the present invention includes a tarajo holly leaf extract and a Japanese knotweed leaf extract, a brown algae extract and an egg shell membrane hydrolysate as its active ingredients.

Tarajo Holly Leaf Extract and Japanese Knotweed Leaf Extract:

The "tarajo holly leaf extract" of the present invention refers to an extract having the tarajo holly leaf as its material. The extract contains flavonoids derived from tarajo holly leaves, which include at least fisetin or its glycoside. The extract may be liquid, or it may be a concentrate, a dried product or a freeze-dried product. The extract may be a mixture of multiple ingredients, or it may be a crude product obtained by purifying the ingredients, a composition containing high purity fisetin (or its glycoside), or an isolated fisetin or its glycoside. The extracts include extracts from water or an aqueous solvent, extracts from organic solvents, such as methanol, ethanol, hexane, and acetone, or extracts from the mixtures of such solvents.

The fisetin structure is shown below.

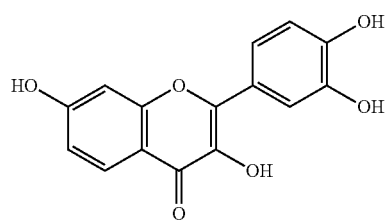

Chemical Formula 1

The method for extracting fisetin is not limited as long as the extract contains sufficient fisetin or its glycoside. A typical extraction is performed by adding ethyl alcohol of 85% or higher, preferably 95% or higher, to the chopped tarajo holly leaves at 10 to 75% (w/v) to the tarajo holly leaves. It is performed at room temperature, for 8 to 72 hours. Specific extraction conditions are presented in the Examples of this specification.

The "Japanese knotweed leaf extract" of the present invention refers to an extract having the Japanese knotweed leaf as its material. The extract contains flavonoids derived from Japanese knotweed leaves, which include at least quercetin or its glycoside. The extract may be liquid, or it may be a concentrate, a dried product or a freeze-dried product. The extract may be a mixture of multiple ingredients, or it may be a crude product obtained by purifying the ingredients, a composition containing high purity quercetin (or its glycoside), or an isolated quercetin or its glycoside. The extracts include extracts from water or an aqueous solvent, extracts from organic solvents, such as methanol, ethanol, hexane, and acetone, or extracts from the mixtures of such solvents.

The quercetin structure is shown below.

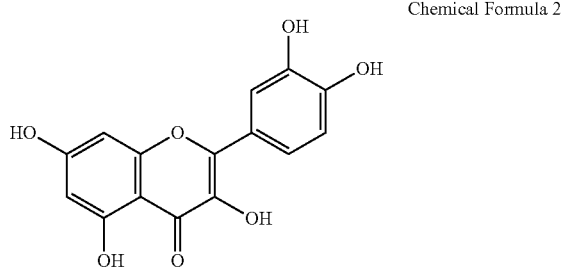 [SMILES: O=c1c(O)c(-c2ccc(O)c(O)c2)oc2cc(O)cc(O)c12]

Chemical Formula 2

The method for extracting quercetin is not limited as long as the extract contains sufficient quercetin or its glycoside. A typical extraction is performed by adding ethyl alcohol of 85% or higher, preferably 95% or higher, to the chopped Japanese knotweed leaves at 10 to 75% (w/v) to the Japanese knotweed leaves. It is performed at room temperature, for 8 to 72 hours. Specific extraction conditions are presented in the Examples of this specification.

Quercetin is known to have antiallergic effects. The investigation by the inventors of the present invention revealed that both the tarajo holly leaf extract and the Japanese knotweed leaf extract show strong histamine release inhibition effects when used alone.

Also the investigation by the inventors of the present invention revealed that both the tarajo holly leaf extract and the Japanese knotweed leaf extract show effects of IL-5 and IL-13 generation inhibition when used alone. Further, this inhibition effect was synergistic for a mixture of the two extracts at a weight ratio of 1:1. The present invention is the first to disclose the synergistic effect of such combination. The external use composition for skin provided by the present invention, which contains a tarajo holly leaf extract and a Japanese knotweed leaf extract, is useful by itself.

The ratio of the tarajo holly leaf extract and the Japanese knotweed leaf extract is not limited in the present invention as long as it induces synergistic effects of the extracts. However, a tarajo holly leaf extract and a Japanese knotweed leaf extract described in the Examples of this specification should be used at 0.1 to 10.0 weight parts, preferably 0.3 to 5.0 weight parts, more preferably 0.5 to 2.0 weight parts of Japanese knotweed leaf extract to 1 weight part of tarajo holly leaf extract. Extracts according to conditions other than the above can be used in amounts corresponding to the above amounts of the extracts of the Examples of this specification. The amounts of other extracts are calculated as necessary by referring to the fisetin or quercetin content.

Also, either the tarajo holly leaf extract or the Japanese knotweed leaf extract or both extracts may be replaced by an extract whose material is leaves, such as persimmon leaves, and leaves of plants in the rose family, which contain flavonoids, mainly quercetin, fisetin, lutein. Such extract can be used similarly to tarajo holly leaf extract or Japanese knotweed leaf extract. The ratio of the respective alternatively used materials can be determined by referring to the fisetin or quercetin content in the tarajo holly leaf extract or the Japanese knotweed leaf extract and adjusting the materials to have an equal fisetin or quercetin content. References are shown below:

Fewtrell, C. M. S. et. al.: Effect of flavone inhibitors of transport ATPase on histamine secretion from rat mast cells. Nature, 265, 635, 1977

Chakravarty, N.: The role of plasma membrane $Ca^{++}$, $Mg^{++}$ activated adenosine triphosphatase of rat mast cells on histamine release. Acta Pharmacol. Toxicol., 47, 223, 1980

Amellal, M. et. al.: Inhibition of mast cell histamine release by flavonoids and biflavonoids. Planta. Med., 1, 16, 1985

Cheong, H. et. al.: Studies of structure activity relationship of flavonoids for the anti-allergic actions. Arch. Pharm. Res., 21, 478, 1998

Kotani, Mayumi et al.: Hito kouenkikyusaibou oyobi mausu ni okeru kaki no ha chuushutubutsu no arerugi yokusei kouka (Allergy Inhibition Effects of Persimmon Leaf Extracts in Human Basophilic Leukocytes and Mouse. Nihon Eiyou/Shokuryoutakkaishi (Journal of Japan Society of Nutrition and Food Sciences), 52(3), 147, 1999

Brown Algae Extracts:

The "brown algae extract" of the present invention refers to an extract having brown algae as its material, specifically a fraction containing at least 250 to 500 molecular mass of cyclooxygenase-2 (COX-2) inhibition substance containing magnesium. The extract may have fucoidan added to it. Fucoidan for use is preferably extracted from brown algae. The COX-2 inhibition substance of 250 to 500 molecular mass is described in detail as CCK in Patent Document 4 listed above. The fraction comprising CCK may be liquid, or it may be a concentrate, a dried product, a freeze-dried product. The extract may be a mixture of multiple ingredients, a crude product obtained by purifying the ingredients, a composition containing high purity CCK, or an isolated CCK or a mixture of one of the above substances and fucoidan.

When fucoidan is added, CCK and fucoidan may be mixed at an appropriate ratio. Fucoidan and CCK described in the Examples of this specification should be used at 1 to 1000 weight parts, preferably 10 to 500 weight parts, more preferably 50 to 200 weight parts of fucoidan to 1 weight part of CCK.

Materials of "brown algae extracts" (or materials of CCK or materials of fucoidan) that can be used in the present invention include seaweeds belonging to the genera *Durvillea*, *Nemacystus*, *Ceratophyllum*, *Lessonia*, *Ecklonia*, *Macrocystis*, *Fucus*, or *Ascophyllum*. More specifically, *Durvillea Antarctica*, *Nemacystus decipiens*, *Ceratophyllum demersum*, *Lessonia nigrescens*, *Ecklonia cava*, Giant Kelp, *Fucus*, *Fucus vesiculosus*, *Ascophyllum nodosum* can be used. Especially preferable seaweeds in view of high specificity to COX-2 are *Durvillea Antarctica* of the genus *Durvillea*, and *Fucus* and *Fucus vesiculosus* of the genus *Fucus*.

If fear exists of seaweeds containing arsenic or other undesirable components, measures can be taken to remove those components.

CCK is extracted typically by chopping dried alga bodies, adding water in an amount 2 to 100 times that of alga bodies, stirring the mixture as necessary, and thermally extracting at 60 to 100° C. for 5 to 60 minutes. The extracted liquid is processed in an ultrafiltration module having an exlusion limit molecular quantity of 1,000. The filtrate is collected and concentrated under reduced pressure and the resulting product is dissolved in ethyl alcohol (final concentration 85% (v/v)). The precipitate is removed from the solution. Then, the solution is decompressed, concentrated, and dried to obtain CCK (refer to Patent Document 4 listed above).

Egg Shell Membrane Derived Peptide (ESM-P):

The "egg shell membrane derived peptide (may be abbreviated to ESM-P)" of the present invention refers to a peptide mixture obtained by hydrolysis of egg shell membranes of birds, preferably chickens. The present invention uses an ESM-P which excludes molecules of molecular masses lower than 3 kDa. The molecules were eliminated by an ultrafilter membrane. Preparation methods known in the conventional art may be used without any particular limitation, but the following method is particularly preferable:

1) Collect egg shells from hen eggs and wash them with water;
2) Add water in an amount 1 to 10 times (w/v) that of the egg shells, and add $BaH_4$ and NaOH so that their final concentrations are respectively 0.1 to 10 mM (preferably 1 mM) and 2 to 50 mM (preferably 20 mM), and process at 60 to 100° C., for 15 to 120 minutes;
3) Collect the aqueous fraction and clarify it by an appropriate process, such as filtration or centrifugation, to exclude the fraction having a molecular mass lower than 3 kDa.

Investigation by the investors of the present invention has revealed that the average molecular mass of the peptide obtained by the above method is about 8 kDa (SDS-PAGE method). The details of amino acids constituting the peptide are shown in the Examples of this specification.

Investigation by the inventors of the present invention has revealed that an ESM-P having a molecular mass of 3 kDa or higher was found to exhibit effects of accelerating filaggrin synthesis.

Active Ingredient Contents:

The composition according to the present invention contains active ingredients in clinically effective doses. The amount of each ingredient when the total composition is 100 weight parts is specifically explained below.

Tarajo holly leaf extracts and Japanese knotweed leaf extracts equivalent to extracts obtained by the method in the Examples of this specification may each be 1 to 20 weight parts, preferably 5 to 15 weight parts, and more preferably 8 to 12 weight parts.

For any blended amount and ratio of tarajo holly leaf extracts and Japanese knotweed leaf extracts, the brown algae extracts equivalent to extracts obtained by the method in the Examples of this specification may be 30 to 90 weight parts, preferably 50 to 85 weight parts, and more preferably 60 to 80 weight parts.

For any blended amount and ratio of tarajo holly leaf extracts and Japanese knotweed leaf extracts, and for any blended amount of brown algae extracts, the ESM-P having molecular masses of 3 kDa or higher equivalent to extracts obtained by the method in the Examples of this specification may be 0.001 to 5.00 weight parts, preferably 0.01 to 1.00 weight parts, and more preferably 0.05 to 0.50 weight parts.

Active ingredients according to other preparation methods can be used in amounts corresponding to those in the Examples of this specification. The amounts of active ingredients according to other preparation methods are calculated as necessary by referring to the contents of the main ingredients including fisetin and quercetin. If all ingredient contents of the subject composition corresponding to the amounts in the Examples of this specification are encompassed in the above ranges, the subject composition is encompassed in the scope of the present invention.

Subjects to Apply the Composition to

Ingredients having the following effects are blended in the present invention: inhibition effects on histamine release from mast cells, and IL-4 and IL-13 generation inhibition effects; selective cyclooxygenase (COX)-2 inhibition effects; and filaggrin synthesis acceleration effects. Diseases or conditions related to a filaggrin metabolism anomaly are triggered by IL-4, IL-13, sphingosyl phosphorylcholine, ROS (a NADPH-oxidase reaction product), and $PGE_2$ (a COX-2 reaction product). To improve symptoms, it is necessary not only to eliminate triggers, but also to normalize filaggrin metabolism.

Accordingly, the composition according to the present invention is useful for treating diseases or conditions related to the filaggrin metabolism anomaly. "Diseases or conditions related to the filaggrin metabolism anomaly" include allergic dermatitis and atopic dermatitis. Causes of the disease include food, drugs, ticks, metal, and animals, without any particular limitation.

When a disease or a condition is "treat(ed)" in the present invention, such action includes reducing the risk of its development, preventing its development, and conducting therapy. Therapy includes nosotropic therapy and etiotropic therapy.

An investigation by the inventors of the present invention produced the following result. When an external use composition for skin containing a tarajo holly leaf extract and a brown algae extract was used, the condition of the atopic dermatitis affected area improved with the application of composition, but the atomic dermatitis symptoms recurred after the application of composition ended. However, when the composition according to the present invention was used, the symptom did not reappear after the application of the composition ended. Hence, the composition according to the present invention is regarded as useful in the therapy of atopic dermatitis, specifically in an etiotropic therapy.

A simple assessment of the composition or each active ingredient of the present invention may use rats and experiment animals or human-derived cells. The composition or each active ingredient may also be assessed by application to actual human patients. The common evaluation standard for the subject disease or condition may be used as the basis of determining whether specific effects exist or not.

Application Methods, Additives, and Other Considerations

The typical daily adult dosage of the composition according to the present invention may be preferably 0.3 to 15,000 mg, more preferably 3 to 1500 mg, and even more preferably 30 to 150 mg. A smaller amount may be effective for prevention or maintenance purposes. A dosage for a day may be given as a single administration or separated into multiple administrations (specifically, two times or three times per a day).

A person skilled in the art can prepare the composition according to the present invention in various dosage forms. Examples of such forms include solutions, emulsions, suspensions, lotions, creams and pastes. The composition can also be in the form of a solid substrate with solutions impregnated therein. Such examples include cataplasms, tapes, and transdermal therapeutic system (TTS) preparations. The composition according to the present invention may be in the form of a kit prepared immediately before use.

Acceptable additives for external use on skin including buffers, emulsifiers, suspending agents, stabilizers, solubilizers, and preservatives may be added to the composition according to the present invention. Aqueous substances and nonaqueous substances gradually separate during storage when no emulsifier is used, but the effectiveness of the composition according to the present invention is unaffected because all its ingredients are quite stable.

The composition according to the present invention may be subjected to various safety verification tests used in the field of art to evaluate whether it is appropriate for the subject or not.

The composition according to the present invention can be used in combination with other ingredients that are effective in the treatment of the subject disease or condition. Ingredients that can be added include hyarulonic acids and rice germ oil.

The composition according to the present invention may be accompanied with indications of details, such as its subject disease or condition, direction for use, and its content. The details can be printed on the container, attached as a label, added as an instruction manual, put in advertisements (including paper medium, electronic medium, posting on websites), explained by a salesperson, or posted on store shelves or areas nearby.

EXAMPLES

Example 1

Evaluation of Each Ingredient

The respective effects of tarajo holly leaf extract and Japanese knotweed leaf extract, brown algae extract, and ESM-P were studied before testing them on human volunteers.

1-1. Tarajo Holly Leaf Extracts and Japanese Knotweed Leaf Extracts:

The tarajo holly leaf extract was obtained by chopping 1,000 g of fresh leaves and adding 95% ethyl alcohol to such leaves to obtain a product with a final concentration of 50% (w/v). The product was maintained by stirring at room temperature for 24 hours, and was clarified by filtration to obtain the liquid extract. Ethyl alcohol was removed from the liquid extract under reduced pressure to obtain about 10 g of yellowish-white/light yellow powders. These powders were used as tarajo holly leaf extracts. LC-MS analysis showed that the percentage of fisetin in the flavonoid contained in this extract is about 15% (w/w).

The Japanese knotweed leaf extract (nature (light brown powder), 15 g) was obtained similarly to the tarajo holly leaf extract. LC-MS analysis showed that quercetin accounts for about 35% (w/w) of flavonoids in the extract.

Abdominal mast cells were collected from an 8 weeks old, male, Wistar/ST rat (Sankyo Labo Service Co.) by the conventional method. They were diluted to $5 \times 10^6$ cells/ml by using sterilized PBS. An 8 weeks old, female, BALB/c mouse was immunized in advance with BSA using ALUM. The titer of the obtained antiserum was measured by the PCA test.

Test substances (tarajo holly leaf extract and Japanese knotweed leaf extract) of concentrations shown in the table below were added in an amount of 100 μl to abdominal mast cells. Subsequently, 100 μl of antiserum (titer 512) was added to the mixture. Then, 100 μl of a 1 mg/ml BSA was added as an antigen to induce an antigen-antibody reaction to release histamine. The reaction supernatant was collected and the amount of histamine was measured using the fluorescence method. The result is shown in Table 1. The inhibition ratios of histamine release from mast cells were 87.8% for a 0.5 mg addition of the test substance, and 88.1% for a 1 mg addition of the test substance. This test substance is one of the most effective histamine release inhibitor in conventionally known plant derived substances.

TABLE 1

Inhibition Ratios of Test Substances against Histamine Release from Rat Abdominal Mast Cells Induced by Antigen-Antibody Reaction

| Test substances | Concentration (mg/ml) | Inhibition ratios of histamine release (%) |
|---|---|---|
| Tarajo Holly Leaf Extract | 0.25 | 65.3 |
|  | 0.50 | 87.8 |
|  | 1.00 | 88.1 |
|  | 10.00 | 88.0 |
| Japanese Knotweed Leaf Extract | 0.25 | 47.5 |
|  | 0.50 | 60.1 |
|  | 1.00 | 75.8 |
|  | 10.00 | 89.2 |

The reaction system containing the cells is 500 μl, so the final concentration (mg/ml) of the test substance is one fifth that in the table.
The histamine release inhibition ratios were calculated as percentages to the control (including no test substance).

Non-B cells and non-T cells were obtained from spleen cells of an 8 week old, male, BALB/c mouse according to the conventional method. The cells were stimulated with solid phased mouse IgE antibody and mouse IL-3 under the presence of tarajo holly leaf extracts or Japanese knotweed leaf extracts and cultured for 36 hours. IL-4 and IL-13 in the culture medium were measured using the ELISA method (Table 2).

The synergistic effect of the combined use was greater than the effect of each extract used alone.

IL-4 and IL-13 Generation Inhibition of Tarajo Holly Leaf Extract, Japanese Knotweed Leaf Extract or their Mixture

|  | IL-4 (pg/ml) | IL-13 (pg/ml) |
|---|---|---|
| Control (IgE antibody and IL-3) | 25 | 410 |
| Tarajo holly leaf extract | 8 | 150 |
| Japanese knotweed leaf extract | 13 | 180 |
| Mixture* | 7 | 110 |

*The mixture was formed with a mixture of equal parts of Tarajo holly leaf extract and Japanese knotweed leaf extract. Each extract was prepared in a concentration of 1 mg/ml, and added to the culture medium. The final concentration each of the extract was 100 μg/ml. The control was prepared in a concentration of 2 mg/ml, and added to the culture medium. The final concentration each of the extract was 200 μg/ml.
The values in the table are averages of six experiments.

1-2. ESM-P:

The egg shell membrane derived peptide (ESM-P) was prepared as follows.

1) The hen eggs were cracked and the obtained egg shells (100 g) were washed with water.

2) Deionized water was added in an amount 2 times that of the egg shells, and $BaH_4$ and NaOH were added so that their final concentrations were respectively 1 mM and 20 mM, and heated at 100° C., for 60 minutes.

3) The aqueous fraction was collected and clarified by an appropriate process, such as filtration or centrifugation, and then the clarified fraction was desalted and concentrated (to about 1:10 (10 times)) by using an UF module (Product name: ultrafiltration (UF) module, model SEP-1013, Manufacturer: Asahi Kasei Chemicals, Co.) having an exclusion limit of 3 kDa.

4) Retentate (molecular mass of 3 kDa or higher) was collected, and freeze-dried (2 g).

The average molecular mass of peptide obtained by the above method is about 8 kDa (SDS-PAGE method, FIG. 1). The amino acids constituting the peptide (amino acid automatic analysis method) are shown in the table below.

TABLE 3

Amino Acid Composition of ESM-P

| Amino Acid | g/100 g |
|---|---|
| Arginine | 2.56 |
| Lysine | 0.99 |
| Histidine | 2.12 |
| Phenylalanine | 1.10 |
| Tyrosine | 1.24 |
| Leucine | 2.96 |
| Isoleucine | 2.10 |
| Methionine(*) | 2.70 |
| Valine | 4.94 |
| Alanine | 2.10 |
| Glycine | 5.20 |
| Proline | 6.14 |
| Glutamic acid | 9.34 |
| Serine | 1.96 |
| Threonine | 1.84 |
| Aspartic acid | 6.20 |
| Tryptophan | 2.24 |
| Cystine(*) | 1.39 |

(*)After oxidation by performic acid, hydrolysis was performed with hydrochloric acid Filaggrin was identified and measured by the following method. Human normal epidermic cells (Kurabo) were seeded in a 24 well plate by allotting $2\times10^5$ cells to each well. The cells underwent preliminary culturing using Humedia-KG2 medium (Kurabo), performed under conditions of 5% $CO_2$ and 37° C., for 24 hours. To the cultured product, ESM-P was added at 0 to 1 mg/ml to the medium. The ESM-P was cultured for 6 days under a condition identical to preliminary culturing.

Cells and extracellular matrices were collected together using a rubber policeman, and filaggrin was identified by the Western Blot Analysis based on unlabeled mouse anti-human filaggrin monoclonal antibody (Santa Cruz Biotechnology, Inc., U.S.A.). Further, the filaggrin amount was measured by a densitometer. Each amount of filaggrin generated by the ESM-P was converted to a ratio to the control to show the corresponding acceleration percentage in Table 4. Each acceleration percentage was obtained from an average of six experiment results.

The filaggrin synthesis acceleration by ESM-P showed concentration dependency, but it plateaued at 0.5 mg/ml and higher. An effect of the egg shell membrane hydrolysate on skin, specifically, a synthesis acceleration effect for extracellular matrix ingredients including collagen and hyaluronic acid, was conventionally known in the art (specifically, Patent Document 3 listed above). However, the effect of egg shell membrane ingredients in accelerating filaggrin synthesis was not known:

TABLE 4

Filaggrin Generation by ESM-P

| ESM-P Concentration (mg/ml) | Filaggrin Generation Acceleration Ratio (%) |
|---|---|
| 0 (Control) | 100 |
| 0.125 | 97 |
| 0.25 | 110 |
| 0.5 | 128 |
| 1.0 | 122 |

1-3. Preparation of Seaweed Extracts:

*Durvillea Antarctica* dried alga bodies (made in Chili, FCC Horiuchi Co.) (100 g) were chopped, and deionized water was added in an amount 20 times that of alga bodies. The mixture was stirred while it was thermally extracted at 85° C. for 20 minutes. A liquid extract was obtained by centrifugation and subjected to ultrafiltration that uses an ultrafiltration module having an exclusion limit molecular quantity of 1,000. The filtrate was collected and concentrated under reduced pressure. Ethyl alcohol was subsequently added to the concentrated product to attain a final ethyl alcohol concentration of 85% (v/v) or higher. A supernatant was obtained by centrifugation, and condensed and dried under reduced pressure (refer to Patent Document 4 listed above). The fucoidan used herein was purchased from Tanglewood Co. A mixture of CCK and fucoidan at a ratio of 1:99 was used as the brown algae extract of Table 5.

Example 2

Evaluation Using Volunteers

Each extract of this embodiment was mixed at a percentage shown in the table below to prepare a lotion.

TABLE 5

Lotion Formulation

| Components | Percentage (%) |
|---|---|
| Tarajo holly leaf extracts | 10 |
| Japanese knotweed leaf extracts | 10 |
| brown algae extracts | 70 |
| ESM-P | 0.1 |
| Hyaluronate | 0.1 |
| Rice germ oil | 3 |
| Water | 6.8 |

Predetermined amounts of tarajo holly leaf extracts, Japanese knotweed leaf extracts, ESM-P, brown algae extracts (Fucoidan, CCK) and sodium hyaluronate (Kewpie Co.) were weighed and mixed, and subsequently dissolved by heating. Then, predetermined amounts of rice germ oil and water were added to the mixture to be emulsified and homogenized using a homomixer. The lotion was yellowish brown and in a milky liquid form. The ingredients used in this volunteer test included neither an emulsifier nor other additives. The lotion was shaken well immediately before its application to form a substantially homogenous mixture.

The lotion was applied to six volunteer adult atopic dermatitis patients (two male, 31 to 47 years old; four female, 26 to 55 years old) for three months. All volunteers had voluntarily limited or rejected the use of therapeutic drugs, and had experiences of attempting various measures from detergents, clothes to living environments. The application amount of the lotion of the present invention was not particularly limited, and the basic usage of the lotion was to apply it to the affected area twice a day, in the morning and in the evening (after bathing in the evening). No other limitation was placed on the volunteers' lifestyle including diets.

The result is shown in the table below. None of the volunteers experienced the reoccurrence of atopic symptoms for at least six months after ending the use of the lotion.

TABLE 6

Volunteer Test

| Volunteer No. | Affected areas | Sensory Assessments and Skin Conditions 3 Months after Application |
|---|---|---|
| 1 (♂) | face, neck, back | In all the volunteers, characteristic itch disappeared immediately after the application, and parts of dry skin peeled off, like skin peeling off when it is sun burnt. The skin when a part of it started to peel off was clean and normal. The renewed skin did not have any characteristic dryness of itch. |
| 2 (♂) | face, hands | |
| 3 (♀) | face, neck | |
| 4 (♀) | face, arms | |
| 5 (♀) | face, inner thigh | |
| 6 (♀) | arms | |

The invention claimed is:

1. A composition consisting essentially of 1 to 20% by weight of a tarajo holly leaf extract, 1 to 20% by weight of a Japanese knotweed leaf extract, 30-90% by weight of a brown algae extract and 0.001 to 5% by weight of an egg shell membrane extracted peptide.

2. The composition of claim 1, wherein the composition is topical.

3. The composition of claim 1, wherein the composition is a solution, emulsion, suspension, lotion, cream or paste.

4. The composition of claim 1, wherein the composition is in the form of a cataplasm, tape or transdermal therapeutic system preparation.

5. A method for treating a subject having a skin disease or condition relating to a filaggrin metabolism anomaly, consisting essentially of administering to the subject an effective amount of the composition of claim 1.

6. The method of claim 5, wherein the composition is administered to the skin of the subject.

7. The method of claim 5, wherein the disease or condition is atopic dermatitis.

8. The method of claim 5, wherein the method reduces or eliminates itchiness or pain.

9. The method of claim 5, wherein the composition is in the form of a solution, emulsion, suspension, lotion, cream or paste.

10. The method of claim 5, wherein the composition is in the form of a cataplasm, tape or transdermal therapeutic system preparation.

\* \* \* \* \*